(12) United States Patent
Rapoport et al.

(10) Patent No.: US 8,807,084 B2
(45) Date of Patent: Aug. 19, 2014

(54) MRI DEVICE WITH A PLURALITY OF INDIVIDUALLY CONTROLLABLE ENTRY PORTS AND INSERTS THEREFOR

(75) Inventors: Uri Rapoport, Moshav Ben Shemen (IL); Itzchak Rabinovitz, New Ziona (IL)

(73) Assignee: Aspect Imaging Ltd., Shoham (IL)

( * ) Notice: Subject to any disclaimer, the term of this patent is extended or adjusted under 35 U.S.C. 154(b) by 189 days.

(21) Appl. No.: 13/241,367

(22) Filed: Sep. 23, 2011

(65) Prior Publication Data

US 2012/0083685 A1    Apr. 5, 2012

Related U.S. Application Data

(60) Provisional application No. 61/387,992, filed on Sep. 30, 2010.

(51) Int. Cl.
*G01R 33/30* (2006.01)

(52) U.S. Cl.
CPC ..................... *G01R 33/30* (2013.01)
USPC ........................................................ 119/417

(58) Field of Classification Search
USPC .................... 119/417, 419, 751, 752
See application file for complete search history.

(56) References Cited

U.S. PATENT DOCUMENTS

| 5,066,915 | A | 11/1991 | Omori et al. |
| 5,167,160 | A * | 12/1992 | Hall, II ..................... 73/864.91 |
| 5,490,513 | A | 2/1996 | Damadian et al. |
| 5,623,927 | A | 4/1997 | Damadian et al. |
| 7,865,226 | B2 * | 1/2011 | Chiodo .......................... 600/407 |
| 2009/0000567 | A1 * | 1/2009 | Hadjioannou et al. ......... 119/755 |
| 2010/0100072 | A1 * | 4/2010 | Chiodo ........................ 604/523 |
| 2010/0269260 | A1 * | 10/2010 | Lanz et al. ........................ 5/601 |

* cited by examiner

*Primary Examiner* — Monica Williams
*Assistant Examiner* — Jessica Wong
(74) *Attorney, Agent, or Firm* — The Law Office of Michael E. Kondoudis

(57) ABSTRACT

An animal handling system for use in a magnetic resonance device (MRD) device, including: a first elongated enclosure having a proximal end, a distal open end and a first geometry, and a second elongated enclosure having a proximal end, a distal open end and a second geometry. The first geometry comprises a first cross-sectional area that is larger than a second cross-sectional area of the second geometry. The first elongated enclosure is inserted into a first input port of the MRD device and the second elongated enclosure is inserted in a second input port of the MRD device diametrically opposite to first input port. When the first elongated enclosure and the second elongated enclosure are inserted into the respective input ports, the second elongated enclosure slides into the first elongated enclosure through the open distal end of the first elongated enclosure.

5 Claims, 6 Drawing Sheets

US 8,807,084 B2

MRI DEVICE WITH A PLURALITY OF INDIVIDUALLY CONTROLLABLE ENTRY PORTS AND INSERTS THEREFOR

FIELD OF THE INVENTION

The present invention generally pertains to an MRI device with a plurality of individually controllable entry ports and inserts therefore.

BACKGROUND OF THE INVENTION

Magnetic resonance imaging (MRI), or nuclear magnetic resonance imaging (NMRI), is primarily a noninvasive medical imaging technique used in radiology to visualize detailed internal structure and limited function of the body. MRI and NMRI devices are examples of a class of devices called magnetic response devices (MRD).

Objects to be analyzed are positioned within an MRI device in a predefined specific location and configuration. It is advantageous to adjust the location of the animal under inspection within the MRI device to obtain optimal analysis. Few patents pertain to means and methods of positioning analyzed objects. Hence for example, U.S. Pat. No. 5,066,915 discloses an RF coil positioning device for an MRI device in which a pallet is movably mounted on a mount and is moved by a drive means so that an RF coil unit mounted on the pallet is moved from its initial position at an imaging position in a magnetostatic field generator, the coil positioning device comprising: coil detecting means provided at a predetermined position along a path of the pallet, for detecting the passage of the RF coil unit through a reference position on the path and generating a detection signal, the distance between the reference position and the imaging position being preknown; distance detecting means for detecting the distance of travel of the pallet; and drive control means supplied with signals from the coil detecting means and the distance detecting means, for controlling the drive means to move the pallet until the distance of its travel after the generation of the detection signal becomes equal to the distance from the reference position to the imaging position; wherein the coil detecting means is provided below the underside of the pallet. Likewise, US patent discloses a diagnostic table for a medical imaging apparatus, the table comprising: a supporting unit; a tabletop movably supported by the supporting unit; a sliding command input device configured to receive a sliding command input, and generate a sliding command instruction corresponding to the sliding command input; a driving device configured to slidably move the tabletop in response to the sliding command instruction; a detector configured to detect actual sliding movement of the tabletop; a controller configured to compare the actual sliding movement of the tabletop with the sliding command instruction, the controller being configured to generate a fault condition instruction when the actual sliding movement of the tabletop is inconsistent with the sliding command instruction; and a stopper provided on the supporting unit and configured to be activated in response to the fault condition instruction in order to inhibit sliding movement of the tabletop. The MRI operator in those MRI systems cannot routinely, quickly and easily switch between one object to another, and between one type of object to other object.

Few patents disclose MRI devices with multiple apertures in the magnet structure. Hence, U.S. Pat. No. 5,490,513 discloses a medical magnetic resonance imaging system comprising: (a) a magnet having an imaging volume and at least two apertures thereto, each of the apertures providing patient access to the imaging volume; (b) at least two patient handling systems, each of the patient handling systems comprising a motorized and remotely-controlled bed structure which accesses a respective one of the apertures of the magnet, each of the bed structures having means for positioning the breast region of a respective patient for a magnetic resonance imaging procedure in the imaging volume of the magnet; (c) a radio frequency antenna system for transmitting radio frequency energy into each of the respective patients when in the imaging volume, and detecting magnetic resonance imaging data from the breast region of each the patient; and (d) automatic patient sequence control means for automatically sequencing the transfer of the respective patients into and out of the imaging volume. Likewise, U.S. Pat. No. 5,623,927 discloses a medical magnet resonance imaging system comprising: (a) a magnet having an imaging volume and at least two apertures, wherein each aperture is sufficiently large to provide patient access to the imaging volume; (b) at least two patient handling systems, with each of the patient handling systems comprising a moveable bed structure having means which provides access to one of the apertures of the magnet and with each of the moveable bed structures having means for receiving and positioning the breast region of a patient to be subjected to a magnetic resonance imaging procedure in the imaging volume of the magnet; (c) a radio frequency antenna system for transmitting radio frequency energy into a patient and detecting magnetic resonance imaging data from the breast region of each the patient. Scanned objects according to those patents are not maneuverable within the MRI device. Fine tuning of the various shape, size and type objects, especially in laboratory routine, wherein a frequent switching of scanned objects of different type shape and size is practically impossible utilizing those MRI systems.

None of the above provides a simple solution for routine insertion of more than one maneuverable small and tangible objects, such as laboratory items (microplates laboratory animals etc), within a single lab-scale experimental MRI device. Hence an MRI device with a plurality of individually controllable entry ports and MRI-compatible inserts therefor fulfill a long felt need.

BRIEF SUMMARY

It is thus one object of the invention to disclose an animal handling system

There is provided in accordance with a preferred embodiment of the present invention an MRD device including a first input port having a first cross-sectional area, and a second input port having second cross-sectional area, the first input port is substantially diametrically opposite the second input port.

Further in accordance with a preferred embodiment of the present invention, the first cross-sectional area is less than the second cross-sectional area.

Still further in accordance with a preferred embodiment of the present invention the first cross-sectional is different from the second cross-sectional area.

There is provided in accordance with another preferred embodiment of the present invention an animal handling system for use in an MRD device including: a first elongated enclosure having a proximal end, a distal open end and a first geometry, and a second first elongated enclosure having a proximal end, a distal open end and a second geometry. The first second geometry includes a first cross-sectional area which is larger than a second cross-sectional area of the second geometry. The first elongated enclosure is inserted into a first input port of the MRD device and the second elongated enclosure is inserted in a second input port of the MRD device diametrically opposite to second input port, such that on insertion of the first elongated enclosure into the first input port and insertion of the second elongated enclosure into the second input, the second elongated enclosure slides into the first elongated enclosure through the open distal end of the first elongated enclosure.

Further in accordance with another preferred embodiment of the present invention the first elongated enclosure includes at least two portions the at least two portions are telescopic.

Still further in accordance with another preferred embodiment of the present invention the proximal end of the first elongated enclosure is sealed against a circumferential edge of the first input port and the proximal end of the second elongated enclosure is sealed against a circumferential edge of the second input port thereby sealing the first and second elongated enclosures from the outside environment.

Additionally in accordance with another preferred embodiment of the present invention a mammal for experimenting is inserted into the second elongated enclosure.

Furthermore in accordance with another preferred embodiment of the present invention the first elongated enclosure includes a reaction testing device.

Further in accordance with another preferred embodiment of the present invention the mammal is selected from the group consisting of a rodent, a cat, a dog, a rabbit and laboratory experimental animals.

DETAILED DESCRIPTION

The following description is provided in order to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for routine handling and scanning of items in a single MRD.

The term 'Magnetic Resonance Device' (MRD) specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) spectroscope or any combination thereof. The MRD hereby disclosed is optionally a portable MRI device, such as devices commercially available from Aspect Imaging (Toronto, Canada), or a commercially available non-portable device. Moreover, the term 'MRD' generally refers in this patent to any medical device configured to accommodate, at least temporarily, an anesthetized animal.

As used herein, the term "animal" or "mouse" refers interchangeably to any living creature, such as neonates, other mammals such as mice, rats, cats, dogs, rabbits etc., and laboratory animals.

As used herein, the term "object" generally refers to items to be scanned, and includes, in a non-limiting manner, laboratory items, such as microplates, microwells, tubes, veils, EPPENDORF tubes and the like, animals, organs, tissues, reaction solutions, cell media, organic or inorganic matter and compositions thereof, etc.

As used herein, the term "plurality" refers in a non-limiting manner to any integer equal to or greater than 1.

Figure 1A:
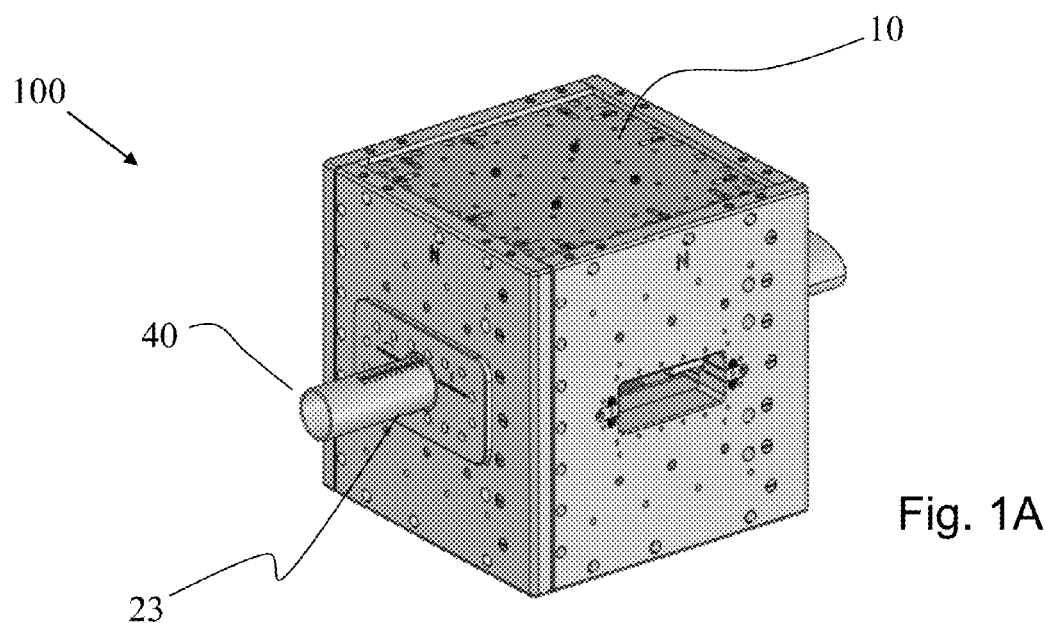
FIG. 1 shows one embodiment of an MRD device comprising two input ports.
Figure 1B:
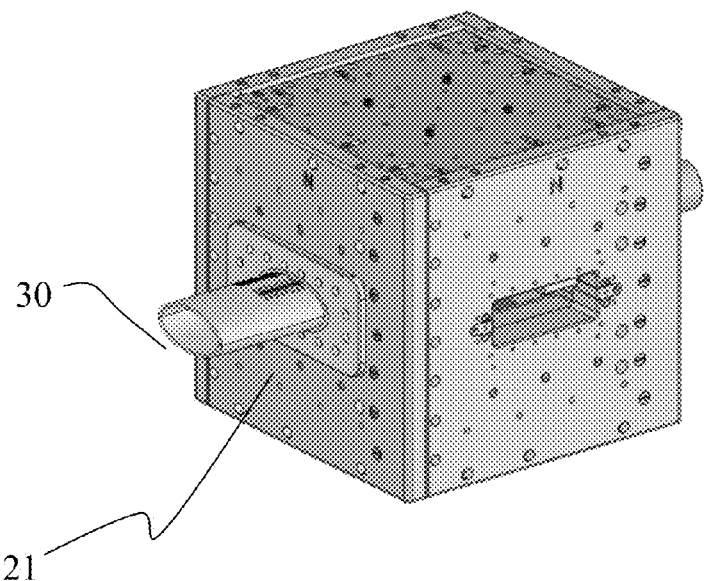

Reference is now made to FIG. 1, schematically illustrating in an out of scale manner an MRD 100, here, a lab-scale MRI device comprising two or more input ports 21 and 23. A plurality of mouse handling systems (MHSs), are reversibly inserted in the input ports. In the embodiments shown, two MHSs 30 and 40, FIGS. 3-4 and FIGS. 5-6, respectively, are reversibly inserted into the respective input ports. The two MHSs 30 and 40 are of different sizes and shapes, and are adapted to be inserted and manipulated for different types of objects to be scanned.

Figure 2:
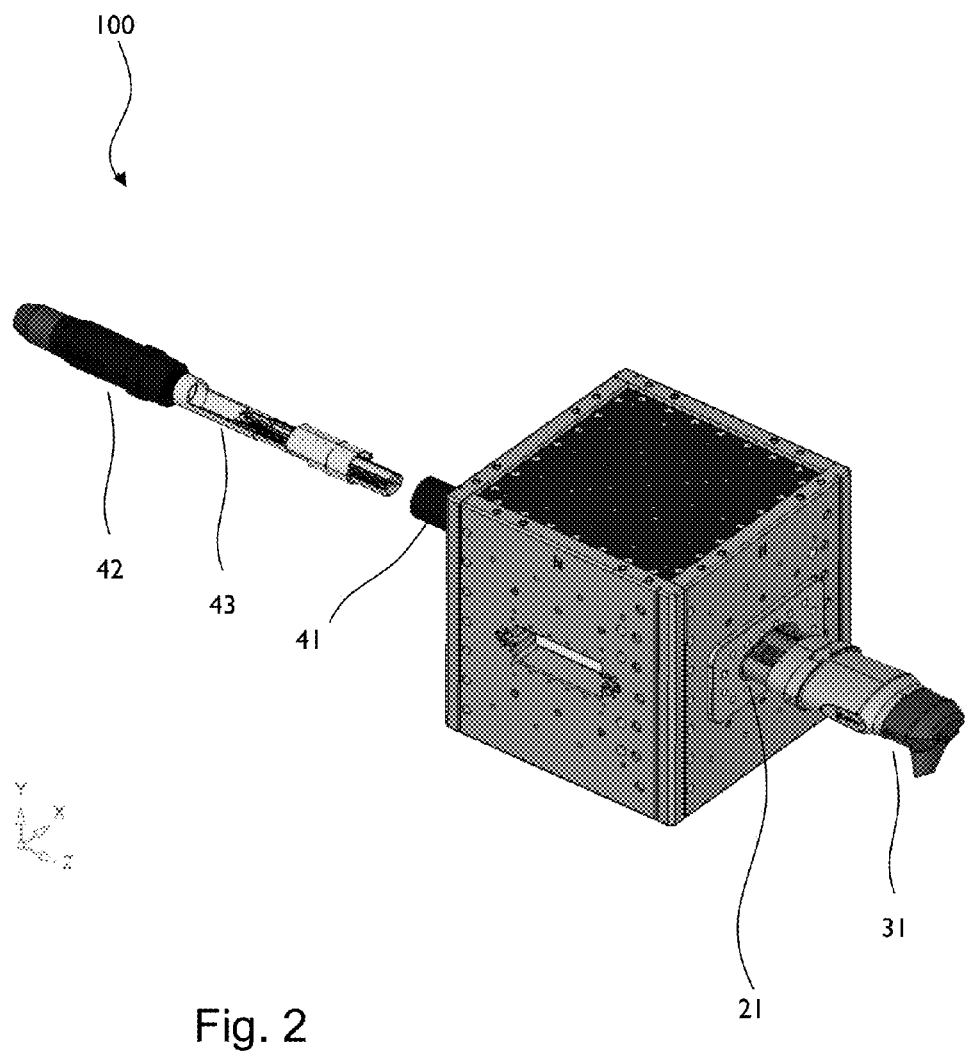
FIG. 2 shows the two Mouse Handling Systems (MHS)

Reference is now made to FIG. 2, schematically illustrating in an out of scale manner MHS 30 and MHS 40. FIG. 2 shows that MHS 30 has an ellipsoidal cross-section and MHS 40 has a circular cross-section. Typically, the circular cross-sectional area of MHS 40 is less than the cross-sectional area of MHS 30. According to the illustrated embodiment of the invention, both MHS 30 and MHS 40 are maneuverable elongated devices. Each one of the MHSs is characterized by a proximal end portion, which is located outside of MRD 10 and possibly comprises an inserting abutment 41. At a distal end portion 43, the objects to be scanned are immobilized in a predefined configuration. The maneuverable MHSs 30 and 40 are rotatable about their respective main longitudinal axes and translatable parallel to shafts 33a and 33b.

Figure 3:
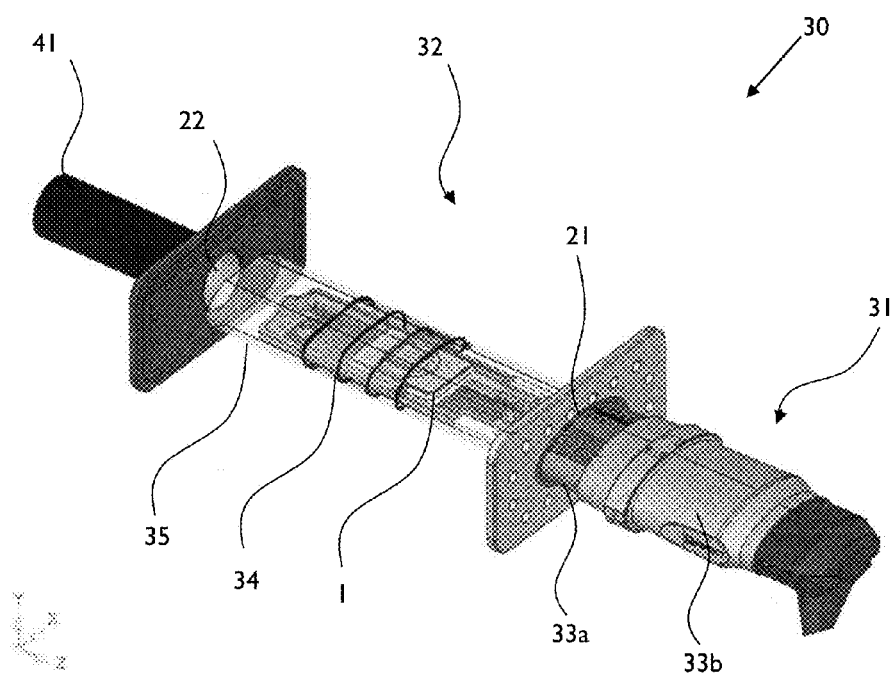
FIGS. 3 and 4 show detailed views of one embodiment of an MHS with an ellipsoidal cross-section.

Reference is now made to FIG. 3, schematically illustrating in an out of scale manner a detailed view of MHS 30. The proximal portion 31 comprises, inter alia, at least one inner shaft 33a and at least one outer shaft 33b, which provide a telescopic maneuvering mechanism for the distal portion 32, located in proximity to input port 21. Positioning of, communication with, and supply to distal portion 32 are performed by means of maneuverable proximal portion 31. The distal portion comprises a support 34, typically of ellipsoidal cross-section and includes a laboratory microplate 1. The microplate 1 includes, inter alia, a plurality micro-wells, which contain reaction media to be scanned. In this embodiment of the invention, the distal portion 32 is at least partially covered by an MRI-compatible envelope 35, thereby preventing leakage of hazardous materials and fluids to the laboratory environment external to the MRD.

Figure 4:
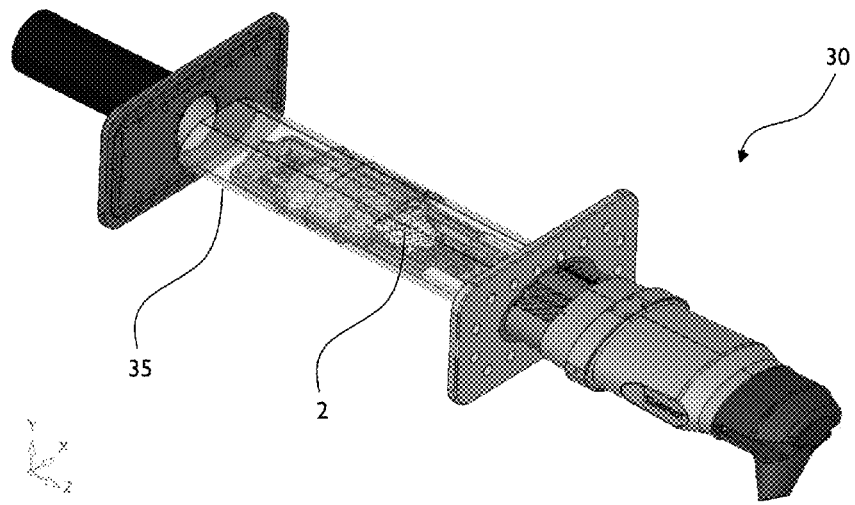

Reference is now made to FIG. 4, illustrating in an out of scale manner a detailed view of MHS 30. FIG. 4 shows that the item to be scanned is a laboratory animal 2, such as a rat.

Figure 5:
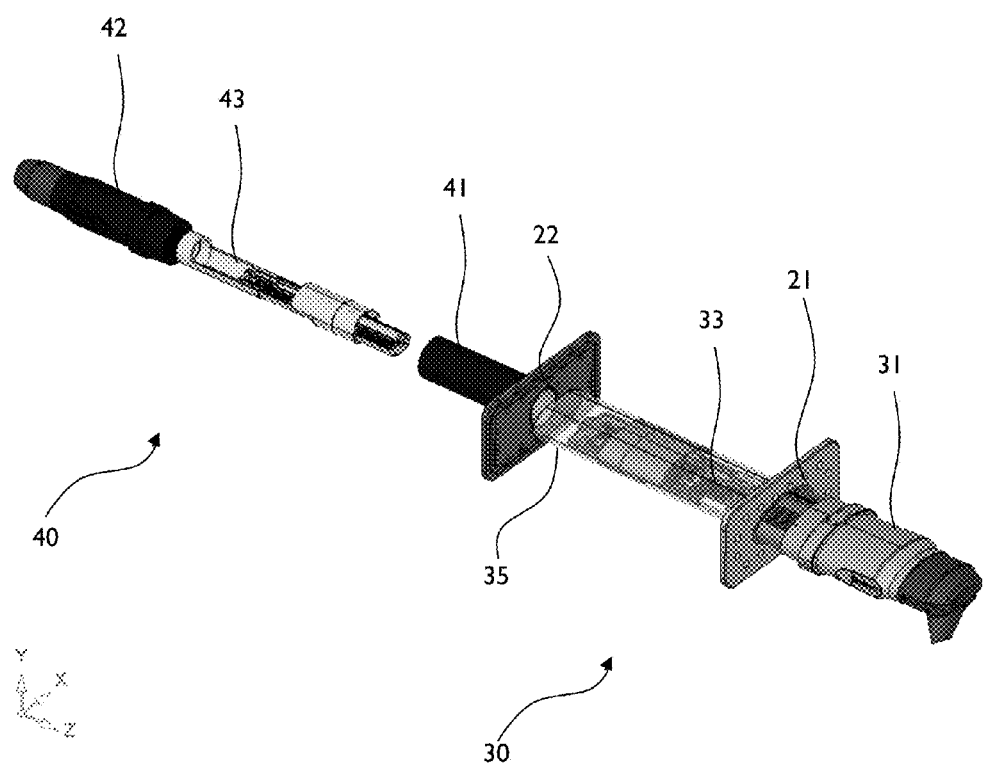
FIGS. 5 and 6 show detailed views of one embodiment of an MHS device with a circular cross-section.

Reference is now made to FIG. 5, schematically illustrating in an out of scale manner a detailed view of MHS 30 and MHS 40. The MRD 10 is schematically presented by means of the two opposite input ports 21 and 22. It is acknowledged in this respect that multiple input ports can be oriented opposite to one another or perpendicular to one another. FIG. 5 shows the easy and quick manner in which different types of MHSs are interchangeable. As described above, MHS 30 is inserted in the MRI device 10 via input port 21. The location of distal portion 32 is controlled from the proximal portion 31. An ellipsoidal cover 35 envelops an inner portion 33 of MHS 30. MHS 40 is inserted into input port 23 such that a distal portion 43 is located within an abutment 41 and coupled to the input port 22. Insertion of the MHS 40 into MHS 30 is thus easily performed.

Figure 6:
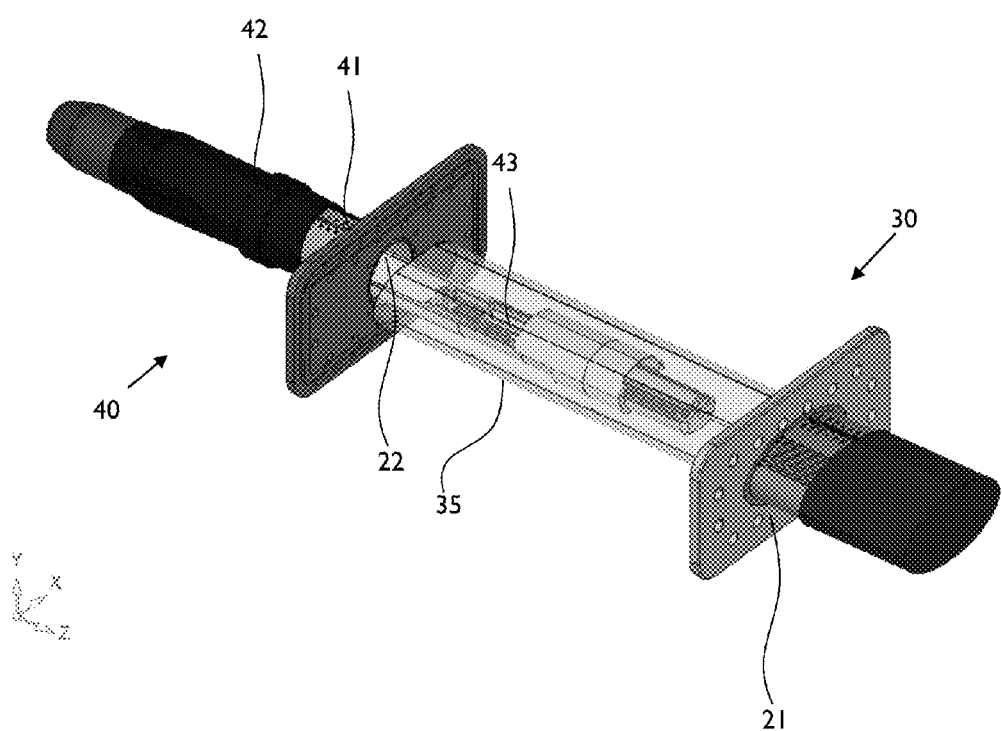

Reference is made to FIG. 6, schematically illustrating in an out of scale manner a detailed view of MHS 40 having a circular cross section, the area of which is typically less than that of the cross-sectional area of MHS 30. MHS 40 is inserted into MRD 10 via input port 22 to within the MRI device 10. A proximal portion 42 manipulates the distal portion 43. Note that distal portion 43 is inserted and encapsulated by the envelope 35. An inserting abutment for MHS 30 seals input port 21.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. An animal handling system for use in an MRD comprising a first input port and a second input port, said animal handling system comprising:
    a first elongated enclosure having a proximal end, an open distal end and a first geometry having a first cross-sectional area; and
    a second elongated enclosure having a proximal end, a distal open end and a second geometry having a second cross-sectional area smaller than said first cross-sectional area,
    wherein said first elongated enclosure is insertable into said first input port and said second elongated enclosure is insertable into said second input port and said second elongated enclosure is slideably insertable into said first elongated enclosure through said open distal end of said first elongated enclosure, and
    wherein said proximal end of said first elongated enclosure is sealed against a circumferential edge of said first input port and said proximal end of said second elongated enclosure is sealed against a circumferential edge of said second input port, thereby sealing the first and second elongated enclosures from the outside environment.

2. The animal handling system according to claim 1, wherein said first elongated enclosure comprises at least two portions said at least two portions are telescopic.

3. The animal handling system according to claim 1, wherein said second elongated enclosure is configured for insertion of an experimental animal.

4. The animal handling system according to claim 3, wherein said experimental animal is selected from the group consisting of a rodent, a cat, a dog, and a rabbit.

5. The animal handling system according to claim 1, wherein said second input port is in a substantially opposite orientation to said first input port.

* * * * *